United States Patent [19]

Lempriere

[11] Patent Number: 4,907,152

[45] Date of Patent: Mar. 6, 1990

[54] METHOD OF IMPROVING CT RESOLUTION

[75] Inventor: Brian M. Lempriere, Renton, Wash.

[73] Assignee: The Boeing Company, Seattle, Wash.

[21] Appl. No.: 281,954

[22] Filed: Dec. 5, 1988

Related U.S. Application Data

[63] Continuation of Ser. No. 911,225, Sep. 25, 1986, abandoned.

[51] Int. Cl.$^4$ .............................................. G06F 15/42
[52] U.S. Cl. ........................... 364/413.18; 364/413.14; 358/213.28; 382/47
[58] Field of Search ........... 364/413.1, 13, 14, 413.17, 364/413.18; 382/6, 41, 47, 27; 358/213.28

[56] References Cited

U.S. PATENT DOCUMENTS

| | | | |
|---|---|---|---|
| 4,127,873 | 11/1978 | Katagi | 358/166 |
| 4,150,401 | 4/1979 | Yamamoto et al. | 358/260 |
| 4,167,039 | 9/1979 | Kowalsi | 364/515 |
| 4,184,206 | 1/1980 | Harano | 364/515 |
| 4,215,414 | 7/1980 | Huelsman | 364/515 |
| 4,231,095 | 10/1980 | Cassagne | 364/515 |
| 4,323,974 | 4/1982 | Sekigawa | 364/515 |
| 4,355,337 | 10/1982 | Sekigawa | 358/284 |
| 4,356,555 | 10/1982 | Ejiri et al. | 364/515 |
| 4,360,883 | 11/1982 | Ijiri et al. | 364/515 |
| 4,381,547 | 4/1983 | Ejiri | 382/47 |
| 4,398,256 | 8/1983 | Nussmeier et al. | 382/41 |
| 4,433,380 | 2/1984 | Abele et al. | 564/414 |
| 4,437,122 | 3/1984 | Walsh et al. | 358/166 |
| 4,484,347 | 11/1984 | Kashioka | 382/47 |
| 4,499,597 | 2/1985 | Alves | 382/41 |
| 4,612,581 | 9/1986 | Endo et al. | 358/213.28 |
| 4,613,986 | 9/1986 | Ataman et al. | 382/27 |
| 4,656,525 | 4/1987 | Morris | 358/284 |
| 4,692,811 | 9/1987 | Tsuchiya et al. | 358/284 |

FOREIGN PATENT DOCUMENTS

| | | | |
|---|---|---|---|
| 0182237 | 5/1986 | European Pat. Off. | 382/47 |
| 2832292 | 2/1980 | Fed. Rep. of Germany | 358/284 |
| 54-136135 | 10/1979 | Japan . | |
| 55-133179 | 10/1980 | Japan . | |
| 0182269 | 9/1985 | Japan | 358/284 |
| 2149994 | 6/1985 | United Kingdom | 358/284 |

OTHER PUBLICATIONS

Wendland, "High Definition Television Studies on Compatible Basis with Present Standard".
P. Stucki, "Optimal Digital Halftone Pattern Generation Method", IBM Technical Disclosure Bulletin, vol. 17, No. 9, Feb. 1975.
A. Appel and C. J. Evangelisti, "Automatic Filling of Bounded Areas in a Raster Display", IBM Technical Disclosure Bulletin, vol. 21, No. 3, Aug. 1978.

*Primary Examiner*—Jerry Smith
*Assistant Examiner*—Kim Thanh Tui
*Attorney, Agent, or Firm*—Christensen, O'Connor, Johnson & Kindness

[57] ABSTRACT

A CT scanning method capable of increased resolution. An object to be scanned is positioned within a CT scanner, and the scanner is operated to perform a first scan to obtain a density value for each of a plurality of first pixels in a planar layer through the object. The scanner is then operated to perform a second scan to obtain a density value for each of a plurality of second pixels in the layer. The second pixels are different from the first pixels, and may be obtained by displacing the first pixels by a translation distance along a translation direction. For a given image element in the layer, a density value is then obtained by averaging the density values of the first and second pixels within which the image element is contained.

7 Claims, 4 Drawing Sheets

| IMAGE ELEMENT | PIXEL FOR FIRST DATA SET | PIXEL FOR SECOND DATA SET | INDIVIDUAL DENSITY VALUES | | DENSITY |
|---|---|---|---|---|---|
| $E_0$ | $P_5$ | $P_{10}$ | 0.75 | 0.75 | 0.75 |
| $E_1$ | $P_2$ | $P_{10}$ | 1.0 | 0.75 | 0.875 |
| $E_2$ | $P_5$ | $P_{12}$ | 0.75 | 1 | 0.875 |
| $E_3$ | $P_4$ | $P_{10}$ | 1.0 | 0.75 | 0.875 |
| $E_4$ | $P_5$ | $P_{11}$ | 0.75 | 1 | 0.875 |
| $E_5$ | $P_1$ | $P_{10}$ | 1.0 | 0.75 | 0.875 |
| $E_6$ | $P_2$ | $P_{11}$ | 1.0 | 1.0 | 1.0 |
| $E_7$ | $P_4$ | $P_{12}$ | 1.0 | 1.0 | 1.0 |
| $E_8$ | $P_5$ | $P_{13}$ | 0.75 | 1.0 | 0.875 |

| IMAGE ELEMENT | PIXEL FOR FIRST DATA SET | PIXEL FOR SECOND DATA SET | INDIVIDUAL DENSITY VALUES | | DENSITY |
|---|---|---|---|---|---|
| E0 | P5 | P10 | 0.75 | 0.75 | 0.75 |
| E1 | P2 | P10 | 1.0 | 0.75 | 0.875 |
| E2 | P5 | P12 | 0.75 | 0.75 | 0.875 |
| E3 | P4 | P10 | 1.0 | 1 | 0.875 |
| E4 | P5 | P11 | 0.75 | 0.75 | 0.875 |
| E5 | P1 | P10 | 1.0 | 1 | 0.875 |
| E6 | P2 | P11 | 1.0 | 0.75 | 0.875 |
| E7 | P4 | P12 | 1.0 | 1.0 | 1.0 |
| E8 | P5 | P13 | 0.75 | 1.0 | 0.875 |

Fig. 9.

METHOD OF IMPROVING CT RESOLUTION

This application is a continuation application based on prior copending application Ser. No. 06/911,225, filed on Sept. 25, 1986 now abandoned.

FIELD OF THE INVENTION

The present invention relates to computed tomography (CT) and, in particular, to a method for increasing the resolution obtainable using a CT scanner.

BACKGROUND OF THE INVENTION

Computed tomography (CT) is a technology that has been extensively developed in recent years in the medical field. A CT scanner is a complex instrument that is capable of measuring density throughout a two-dimensional plane passing through a patient or other object. By performing a CT scan along multiple planes displaced from one another in a direction normal to the planes, information concerning density throughout a three-dimensional portion of a patient's body may be obtained.

One nonmedical application for which medical CT scanners are well suited is the nondestructive testing of objects fabricated from materials having densities approximately equal to the density of the human body. One example of such an object is a rocket nozzle fabricated from a carbon-carbon composite. The production of such a nozzle involves a lengthy process that starts with graphite cloth impregnated with phenolic resin, and that includes one or more graphitization steps in which the nozzle is subject to temperatures of 4500° F. Because of the length of a carbon-carbon production process, it is extremely important that the nozzle be inspected for defects at a number of stages in the process. In the past, such defect inspection has primarily been accomplished by means of tangentially directed X-rays.

In a typical tangent X-ray technique, an X-ray source is located approximately six feet from the nozzle, and a film cassette is positioned adjacent the nozzle behind the area of interest. The nozzle is exposed to X-rays from the source for a time period ranging from 35–90 seconds, and the film is then developed. The defects that are of interest, such as wrinkles, foldbacks and porosity, show up in the film as density variations that are referred to as low-density indications (LDIs). The tangent X-ray technique can detect LDI's only if they extend over a long enough path length to cause a difference in X-ray beam attenuation of 2–4 percent. For this reason, only LDIs that are in line with the tangent X-ray beam will be detected. This results in a number of defects remaining undetected unless a large number of tangent angles are selected. In practice, a compromise between complete inspection and representative inspection is usually selected.

The development of X-ray computed tomography during the past 10 years for medical applications has produced the technological breakthrough required for more effective nondestructive evaluation and inspection of carbon-carbon material. The low energy X-ray CT technology developed for medical application on the human body is directly applicable to carbon cones, and provides quantitative density data in addition to qualitative pictures. In particular, a CT system is capable of providing a direct measure of the bulk density of a nozzle or other object at any point of interest, rather than simply along selected lines or tangents. Furthermore, a CT system, unlike photographic film, provides an extremely wide dynamic range that allows density measurements with a resolution of 0.1%.

SUMMARY OF THE INVENTION

The present invention provides a method for operating a CT scanner so as to increase the resolution obtainable through the use of the scanner without incurring the expense and complexity of a refined sensor system. In particular, the method is capable of determining the density of an object within one or more image elements lying in a planar layer extending through the object, wherein the image elements may in general be smaller than the pixel size (i.e. resolution) of the CT scanner.

In a preferred embodiment, the method comprises operating the CT scanner to perform first and second scans, and then combining the data produced by the scans to obtain improved resolution density values. The first CT scan produces a density value for each of a plurality of first pixels in the scanned layer. The second scan produces a density value for each of a plurality of second pixels in the layer, the second pixels being different than the first pixels. In a preferred embodiment, the second pixels are obtained by displacing the first pixels by a translation distance along a translation direction. Once the first and second scans have been performed, density values are obtained for image elements by an averaging process. In particular, for each image element, the density value is taken to be the average of the density values obtained for the first and second pixels within which the image element is contained.

BRIEF DESCRIPTION OF THE DRAWINGS

FIG. 9 is a table showing the combination of data sets to produce improved resolution density values;

DETAILED DESCRIPTION OF THE INVENTION

Figure 1:
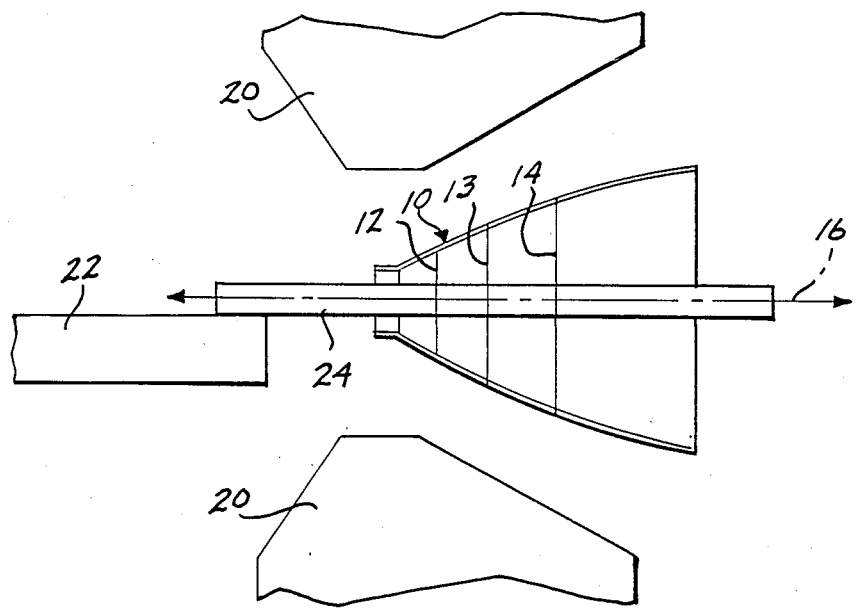
FIG. 1 is a schematic view of a portion of a CT scanner in which a rocket nozzle has been positioned for nondestructive testing.

FIG. 1 schematically illustrates the application of a medical CT scanner, such as a GE 9800 Computed Tomography Scanner, to the nondestructive testing of a rocket nozzle. In FIG. 1, nozzle 10 may be inspected at any number of layers 12, 13 and 14 that pass through the nozzle in a direction normal to axis 16. The CT scanner is schematically illustrated as comprising toroidal gantry 20, bed 22, and support fixture 24. Gantry 20 includes the X-ray source and the detectors, and is adapted to rotate about axis 16. Bed 22 is normally used for supporting a patient, and the CT scanner includes means for accurately positioning the bed with respect to the gantry along the direction of axis 16. Support fixture 24 is shown schematically in FIG. 1, and is adapted to be translated horizontally along with bed 22, and to support nozzle 10 such that the central symmetry axis of the nozzle coincides with axis 16. The right hand end of fixture 24 would also typically be supported by any suitable horizontally translatable means to add rigidity to the nozzle support structure.

Figure 2:
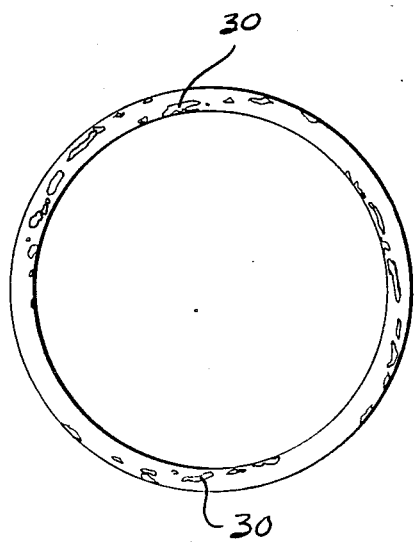
FIG. 2 is a representative view of the result of a CT scan through one plane of the nozzle.
Figure 3:
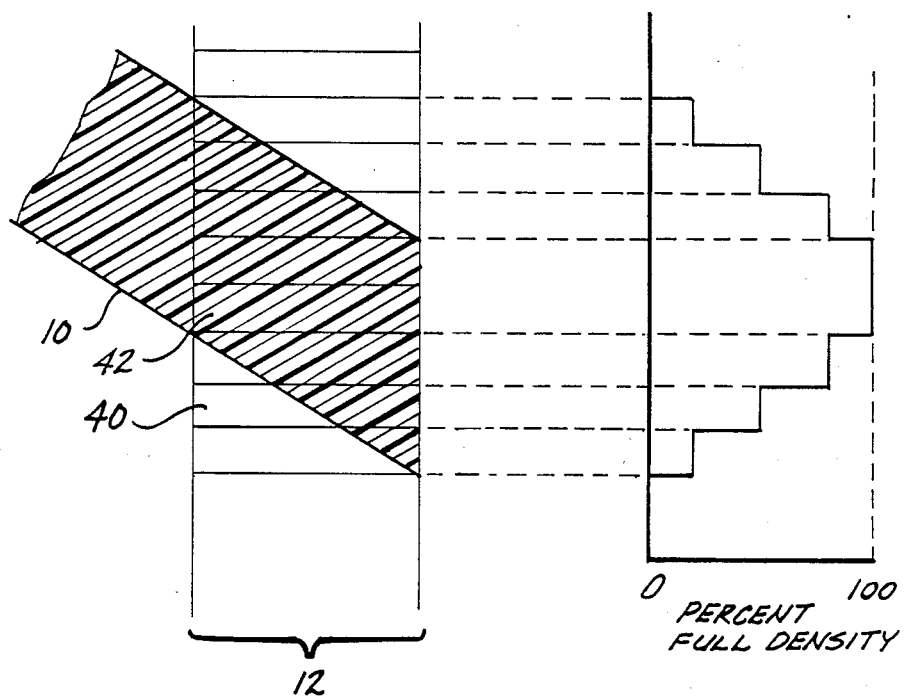
FIG. 3 is an illustration of the partial volume effect in CT scanning.

The result of a typical scan is shown in FIG. 2, wherein LDIs 30 may be observed. In general, the display of a CT scan may be enhanced by using a gray scale, such as an eight-shade gray scale, in contrast to the black/white scale used in FIG. 2. Each picture element ("pixel") in each plane of a CT scan corresponds to a volume element of a certain size within the nozzle, the volume element having an area equal to the pixel area and a height equal to the thickness of the layer. The pixel size does not represent the lower limit of the size of the defect that can be seen. A smaller defect will appear in the CT image with reduced contrast as long as the density contrast of the defect is sufficient. This is known as the "partial volume" effect, and is generally illustrated in FIG. 3. FIG. 3 illustrates plane 12 through a portion of nozzle 10. The CT scanning operation divides planar layer 12 into a plurality of pixels 40, each of which extends through the layer in a direction perpendicular to the plane of the layer. Assuming that nozzle 10 has uniform density within the areas shown in FIG. 3, the density measured for each pixel depends upon the fraction of the pixel volume that is occupied by the nozzle material. The right hand side of FIG. 3 illustrates the densities that would be measured for various pixels. The density variations would show up as gray-scale variations in a two-dimensional image of layer 12. in a similar manner, if one of the pixels contained entirely within nozzle 10, such as pixel 42, included a low-density volume, then the density measured for that pixel would be less than the full density, and could therefore be detected even though the low density volume was smaller than a pixel volume. Despite the fact that defects smaller than a pixel can be detected in a CT system, the pixel size does limit precision in determining the positions of small features.

During the inspection of carbon-carbon composites using a CT scanner, the need has arisen to improve the spatial resolution so as to more readily detect and locate low-density areas in the composites. The size of a pixel, which limits the resolution, is determined by the size of the CT scanner and the number of its detectors. Previous attempts at improving resolution have concentrated primarily on hardware developments, such as increasing the number of detectors. However, such developments are constrained by a number of limitations, such as size, cost, and scanning time.

In accordance with the present invention, a technique has been developed for improving the resolution of a CT scanner, such that the position of defects can be more accurately located. The method involves making multiple CT scans for each layer, such as layer 12 of nozzle 10 shown in FIGS. 1 and 3. In particular, in one preferred embodiment of the invention, two CT scans are made for each layer. First, a scan is made in a conventional manner with the nozzle located at a predetermined position with respect to the CT scanner. The result of this scan is a first data set comprising a density value for each pixel within the scanned layer. The nozzle is then displaced along a direction parallel to the plane of the layer, for a displacement distance that is smaller than the distance between the centers of adjacent pixels. A second CT scan is then performed, producing a second data set of density values. The layer is then imagined as being divided into a plurality of image elements that are smaller than pixels. In a typical embodiment, the linear dimensions of each image element are one-half of the linear dimensions of the pixels, such that a single pixel includes four image elements. For each image element, a density value is then determined by averaging the density values for the two pixels (one in the first data set and one in the second data set) that include the image element. The result is a higher resolution density map of the plane of interest.

Figures 4, 5:
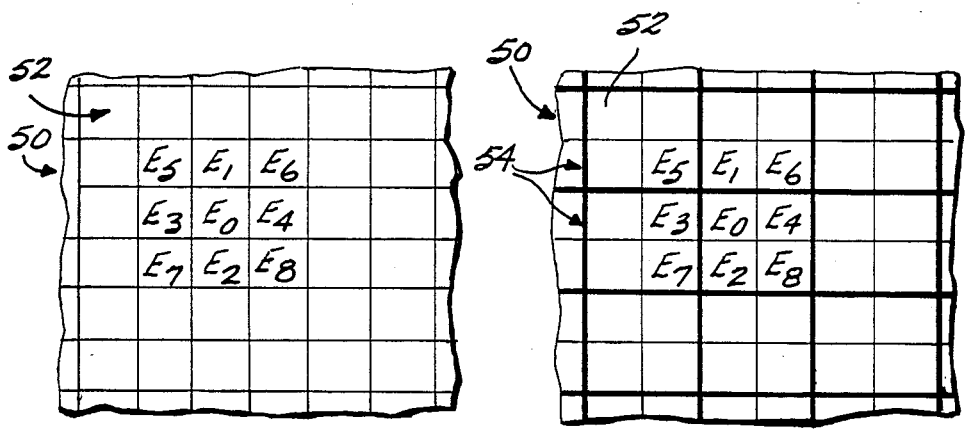
FIGS. 4–8 illustrate the collection of pixel density data in accordance with the method of the present invention.

The technique of the present invention can be described by means of an example. Referring to FIG. 4, reference numeral 50 designates a thin planar layer through an object of interest that is to be analyzed by means of a CT scanner. In FIG. 4 and in subsequent Figures, the layer is parallel to the plane of the drawing. Layer 50 is divided into an array of image elements 52, a total of 36 image elements being shown in FIG. 4. Each image element has a square cross section and extends through layer 50 from its upper to lower surface. The linear dimensions of each image element 52 in layer 50 are selected to be equal to half of the pixel size of the CT scanner, for reasons set forth below. In FIG. 4, nine individual image elements $E_0$–$E_8$ have been identified. The technique of the present invention will provide density values for each image element 52, despite the fact that each of such image elements covers an area smaller than the nominal miminum resolution (i.e., the pixel size) of the CT scanner.

Figure 6:
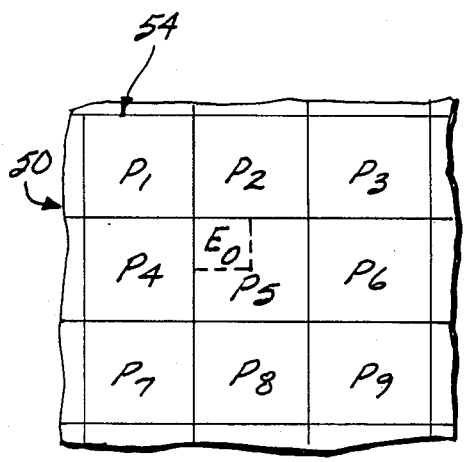

In accordance with the present invention, the object of interest is positioned within a CT scanner, and the scanner is operated to obtain a set of density values for layer 50. The resolution of the CT scanner is such that a density value can be determined for a series of pixels, where each pixel has an area and volume equal to the combined area and volume of four image elements. Without loss of generality, it will be assumed that the boundaries between adjacent pixels are aligned with the boundaries between adjacent image elements. FIG. 5 illustrates the relationship between pixels 54 (in heavy lines) and image elements 52 (in light lines). The nine pixels shown in FIG. 5 will be designated by $P_1$–$P_9$, as illustrated in FIG. 6. FIG. 6 illustrates the location of image element $E_0$ in relation to the pixels.

It will be assumed that image element $E_0$ corresponds to a void area of zero density, and that all surrounding image elements are positioned in areas or volumes of nominal density for the material, which will be taken as equal to 1.0 for the purpose of the present example. The first step in the method of the present invention is to operate the CT scanner so as to produce a first data set for pixels $P_1$–$P_9$. Inspection of FIG. 6 indicates that the first data set will comprise a density value of 0.75 for pixel $P_5$ and density values of 1.0 for all other pixels.

Figure 7:
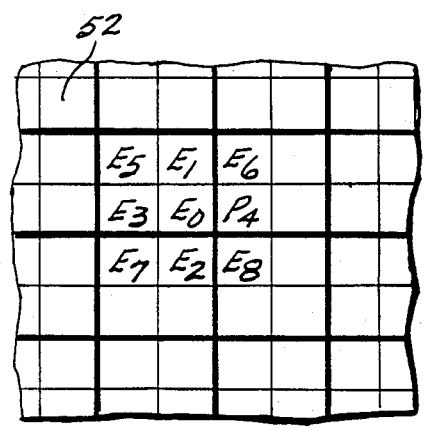
Figure 8:
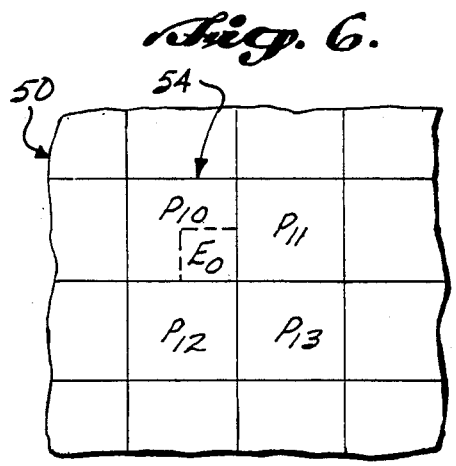

The second step of the present invention comprises translating the object under test with respect to the CT scanner in a direction parallel to plane 50 for a distance of half of the dimension of a pixel, and then repeating the CT scan to collect a second data set. For the present illustration, it will be assumed that the translation is in a diagonal direction, i.e., in a direction oriented 45° C. with respect to the boundaries between adjacent pixels. It will further be assumed that the translation distance is equal to one-half of the length of the diagonal of each pixel. As a result, the relationship between image elements 52 and the new pixels will be as indicated in FIG. 7. It can readily be seen that the relationship between image elements and pixels shown in FIG. 7 will be obtained regardless of which diagonal is selected for translation, and regardless of the translation direction along the selected diagonal. FIG. 8 illustrates four pixels $P_{10}$–$P_{13}$ for which data is collected in the second data set. The position of image element $E_0$ with respect to pixels $P_{10}$–$P_{13}$ is also illustrated in FIG. 8. As a result of this relationship, a density measurement of 0.75 will be obtained for pixel $P_{10}$, while density values of 1.0 will be obtained for all other pixels in the second data set.

Figure 10:
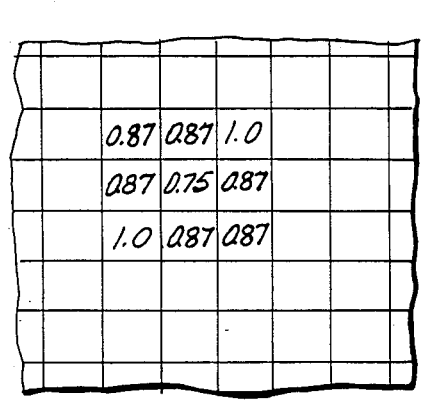
FIGS. 10–11 illustrate the density values produced by the method of the present invention.

FIG. 9 is a table that illustrates the relationship between image elements and pixels for the first and second data sets. For example, image element $E_0$ is in pixel $P_5$ for the first data set (FIGS. 5 and 6), and is in pixel $P_{10}$ for the second data set (FIGS. 7 and 8). In accordance with the third step of the present invention, each image element $E_0$–$E_8$ is assigned a density value that is equal to the average of the density values measured for all pixels within which the image element is contained. Thus for image element $E_0$, the density value obtained is the average of the density values obtained for pixels $P_5$ and $P_{10}$, i.e., a density value of 0.75. In a similar manner, image element $E_1$ is assigned a density value of 0.87 that is equal to the average of the density values obtained for pixels $P_2$ (1.0) and $P_{10}$ (0.75). FIG. 10 is a graphical illustration of the results shown in the last column of FIG. 9. As can be seen from FIG. 10, the location of zero density image element $E_0$ has been accurately determined, despite the fact that the resolution of the CT scanner would not otherwise permit such location to be determined. It can readily be verified that the asymmetry between image elements $E_5$ and $E_8$ on the one hand, and $E_6$ and $E_7$ on the other hand, is an artifact resulting from the location of image element $E_0$ with respect to the pixels.

Figure 11:
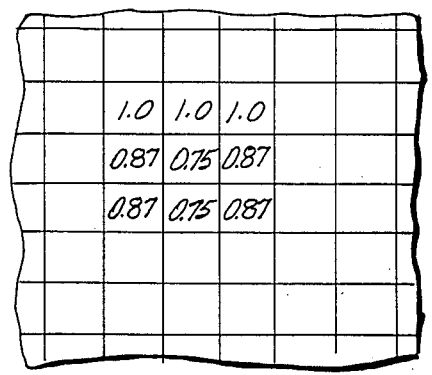

The method of the present invention does not require a predetermined direction of translation with respect to the image element and pixel boundaries. For example FIG. 11 illustrates the result of shifting the pixels horizontally between the first and second data sets for a distance equal to half the linear dimension of each pixel. Although the improvement and resolution is not as great in this case as in the example of FIG. 10, it can nevertheless be observed that the location of the defect has been determined to within an area comprising two image elements, as compared to the four image element area obtained without the use of the present invention. Also as with FIG. 10, it can readily be confirmed that the asymmetry shown in FIG. 11 as between image elements $E_5$, $E_1$, and $E_6$ on one hand, and $E_7$, $E_2$, and $E_8$ on the other hand, is an artifact resulting from the location of image element $E_0$ with respect to the pixels. A result entirely analogous to that shown in FIG. 11 would be obtained for vertical translation between collection of the first and second data sets.

For the described embodiment in which two scans were used and in which all pixels had identical sizes and shapes, a preferred translation distance is one-half the distance between pixels. Stated differently, the preferred translation distance is selected such that if two of such translations were performed, the original pixel pattern would be obtained. In general for embodiments in which N scans are performed, the preferred translation distance between successive scans is 1/N of the average spacing between pixels, and the translation direction is constant, so that once again N individual translations would restore the original pixel pattern.

While the preferred embodiments of the invention have been illustrated and described, it is to be understood that variations will be apparent to those skilled in the art. For example, the averaging step need not utilize unweighted linear averaging as in the illustrated embodiment, and weighted and/or nonlinear (e.g., geometric) averaging may be used where appropriate. Accordingly, the invention is not to be limited to the specific embodiments illustrated and described, and the true scope and spirit of the invention are to be determined by reference to the following claims.

I claim:

1. A method for determining the density of an object within at least one image element lying in a planar layer of the object, the method comprising:

positioning the object within a CT scanner, and operating the CT scanner to perform a first scan to obtain a density value for each of a plurality of first pixels in the layer such that one of the first pixels fully contains the image element;

causing relative movement between the CT scanner and object in a direction parallel to the planar layer;

operating the CT scanner to perform a second scan to obtain a density value for each of a plurality of second pixels in the layer such that one of the second pixels fully contains the image element, the second pixels being displaced with respect to the first pixels by said relative movement such that the image element has a different position relative to the first pixels than to the second pixels; and, determining a density value for said image element by averaging the density value of the first pixel that fully contains the image element and the density value of the second pixel that fully contains the image element.

2. The method of claim 1, wherein the first and second scans are performed such that all first pixels have the same area and such that all second pixels have the same area.

3. The method of claim 2, wherein the first and second scans are performed such that all first and second pixels have the same area.

4. The method of claim 3, wherein the second pixels comprise the first pixels displaced by a translation distance along a translation direction.

5. The method of claim 4, wherein along the translation direction, the centers of the first pixels are spaced apart from one another by a predetermined pixel spacing, and wherein the translation distance is less than said pixel spacing.

6. The method of claim 5, wherein the pixels are rectangular, and wherein the translation direction is parallel to a line drawn between opposite corners of one of the first pixels.

7. The method of claim 6, wherein the translation distance is equal to approximately half of the length of said line.

* * * * *